United States Patent [19]

Tetsuro et al.

[11] 4,338,301
[45] Jul. 6, 1982

[54] LUNG TISSUE EXTRACT USEFUL FOR TREATING HYALINE-MEMBRANE DISEASE AND METHOD FOR PRODUCING THE EXTRACT

[75] Inventors: Fujiwara Tetsuro, Akita; Tanaka Yuji, Toda; Takei Tsunetomo, Kuki, all of Japan

[73] Assignee: Tokyo Tanabe Co., Ltd., Japan

[21] Appl. No.: 152,048

[22] Filed: May 21, 1980

[30] Foreign Application Priority Data

Jun. 2, 1979 [JP]  Japan .................................. 54-68211

[51] Int. Cl.$^3$ ............................................. A61K 35/12
[52] U.S. Cl. ....................................................... 424/95
[58] Field of Search ................................... 424/95, 199

[56] References Cited

PUBLICATIONS

King et al., Am. J. of Physiol, vol. 223, No. 3, Sep. 1972, pp. 707–726.
Adams et al., Pediat. Res., vol. 12, (1978), pp. 841–848.
Harwood et al., Biochem. J., vol. 151, (1975), pp. 707–714.
Onophrio, Chem. Abst., vol. 79, (1973), p. 96957x.

*Primary Examiner*—Sam Rosen
*Attorney, Agent, or Firm*—McGlew and Tuttle

[57] ABSTRACT

A surface active material may be produced from the lung tissue of mammal by means of employing an acetone-treatment procedure as well as an organic solvents mixture-treatment procedure other than the conventional procedures of differential centrifugation, density gradient centrifugation and dialysis. The chemical composition of the active material has for example, a phospholipid content of 75.0–95.5%, a neutral lipid content of 1.8–14.0%, total cholesterol content of 0.0–3.0%, carbohydrate content is 0.1–1.5% and protein content is 0.5–5.0%, all based on the dried weight of the material. The pharmaceutical composition containing the surface active material defined as above is usable for clinical treatment of human hyaline-membrane disease.

23 Claims, 3 Drawing Figures

LUNG TISSUE EXTRACT USEFUL FOR TREATING HYALINE-MEMBRANE DISEASE AND METHOD FOR PRODUCING THE EXTRACT

FIELD AND BACKGROUND OF THE INVENTION

The present invention relates to a surface active material having a new chemical composition, method for producing the same and pharmaceutical composition usable for treating hyaline-membrane disease containing the active material.

The lung of a mammal performs, as is generally known, the respiration function that imbibe atmospheric oxygen into its blood and discharge carbon-dioxide gas therefrom through the cells consisting of intra-surface of many lung alveoli (i.e., cavity portion of lung) which are connected to the trachea or airway. Virgorous investigations in recent years with respect to lung physiology, particularly to the respiratory troubles in premature infant of short gestation period, have elucidated that there is a specific material in lung alveoli that lends to the stability of the liquid-air interface therein (generally called pulmonary surfactant). The deficiency of this material causes problems in respiratory function or the so-named hyaline-membrane disease (hereinafter abbreviated HMD). Different opinions however, have been reported on the precise chemical nature, especially chemical composition, of such pulmonary surfactant which have been extracted from a living body.

For the treatment of HMD, there have hitherto been employed the so-called continuous positive airway pressure method in which air or oxygen is forced into the airway of patient through a thin pipe of polyvinyl. Another method for promoting fetal lung maturation is by administering specific steroid compounds to the mother. There also has recently been reported a method of supplementing phosphatidylcholine and phosphatidylglycerol, both of which are demonstrated as main components of the pulmonary surfactant, by instilling them into the airway [cf. Summary of Lecture Meeting of Pediatric Research Society, Atlantic City, 1970, P84; Pediatrics, 48, 547, 1971; Pediatric Research, 11, 573, 1977]. Although these conventional methods for treatment of HMD have exhibited some effect, they have not yet been regarded as producing fundamental effect.

The pulmonary surfactants extracted from the lung of mammals other than human, unavoidably contain a considerable amount of so-called foreign proteins and are contaminated generally with microorganisms, so that it is not practical to use such surfactants for the clinical treatment of human HMD.

The chemical composition of conventional pulmonary surfactants has been regarded generally as being 10–20% of protein and 80–90% lipid both based on the whole surfactant, which lipid consists of about 10% neutral lipid (e.g., triglyceride, cholesterol) and of about 90% phospholipid both based on the same, while the phosphatidylcholine content based on the total phospholipid is 86%. In this specification and claims, both "%" and "part" are on the dried matter basis unless otherwise indicated.

SUMMARY OF THE INVENTION

We have studied a material which is capable of being employed in clinical treatment on human HMD, and found that the surface active material which was extracted from the lung tissue of mammals by means of employing the combination of acetone-treatment procedure and organic solvents mixture-treatment procedure other than the conventional procedures of differential centrifugation, density gradient centrifugation and dialysis and which had a new chemical composition of less protein content as well as high content of phosphatidylcholine having two saturated fatty acid residues, exhibited significant reduction of surface tension in human lung alveolar space to result in a clinical effect of HMD, without suffering from the foreign proteins.

According to one feature of the present invention there is provided a surface-active material which is extracted from the lung tissue of mammals and the chemical composition of which is such that the phospholipid content is 75.0–95.5%, the neutral lipid content is 1.8–14.0%, the total cholesterol content is 0.0–3.0%, the carbohydrate content is 0.1–1.5% and the protein content is 0.5–5.0%, all based on the dried weight of the surface active material. A portion of the phospholipid may, if necessary, consist of newly added or further phospholipid.

According to a further feature of the present invention there is provided a method for producing the surface active material as defined above which comprises the steps of bringing small pieces of lung of a mammal into contact with an electrolyte solution, taking up a crude surface active material from the resulting extract, and supplementing a required amount of additional phospholipid thereto so that the phospholipid content may be 75.0–95.5% based on the total active material.

According to a still further feature of the present invention there is provided a pharmaceutical composition usable for HMD containing the surface active material as defined above.

For an understanding of the principles of the invention, reference is made to the following description of typical embodiments thereof as illustrated in the accompanying drawings.

DESCRIPTION OF THE PREFERRED EMBODIMENTS

Figure 1:
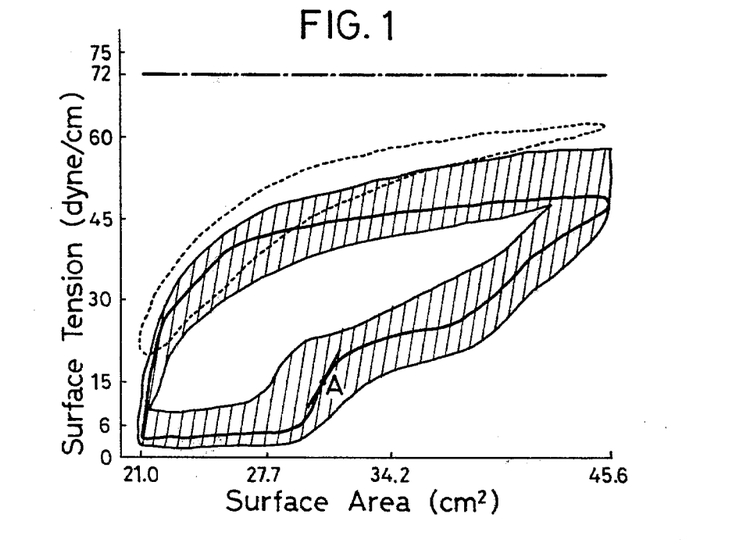
FIG. 1 is a hysteresis curve showing surface-tension plotted against surface area of a mammalian lung.

FIG. 1 illustrates the relation diagrams (or so-called hysteresis curves) of surface tension-surface area of the physiological saline used for the test. The shaded portion in FIG. 1 indicates the region into which hysteresis curves will fall when the active material of the invention has been added, dropwise, to the surface of physiological saline in an amount of 0.3–0.8 $\mu$g per square centimeter of surface area (the bold solid line represents an example of such hysteresis curves). The chain line represents such a hysteresis curve where no active material has been added. The dotted line represents the hysteresis curve when 0.5 $\mu$g of dipalmitoylphosphatidylcholine-phosphatidylglycerol mixture (weight ratio of 9:1) has been added dropwise per square centimeter of surface area. The surface tension was measured at 15°–25° C. and recorded by using an Acoma Wilhelmy surface tension balance and X-Y recorder, Model F-3D (mfd. by Acoma Igaku Kogyo Co., Ltd. and Riken Denshi Co., Ltd., respectively).

Figure 2:
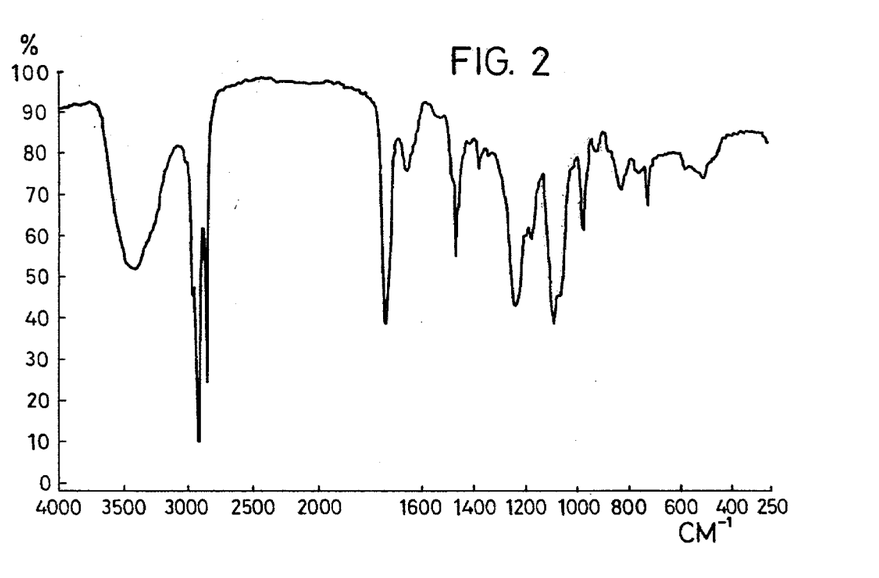
FIG. 2 is an infrared absorption spectrum of the inventive material.

FIG. 2 illustrates the infrared absorption spectrum of the active material of the invention as measured in a KBr tablet with infrared spectrophotometer, Hitachi 295 Model.

Figure 3:
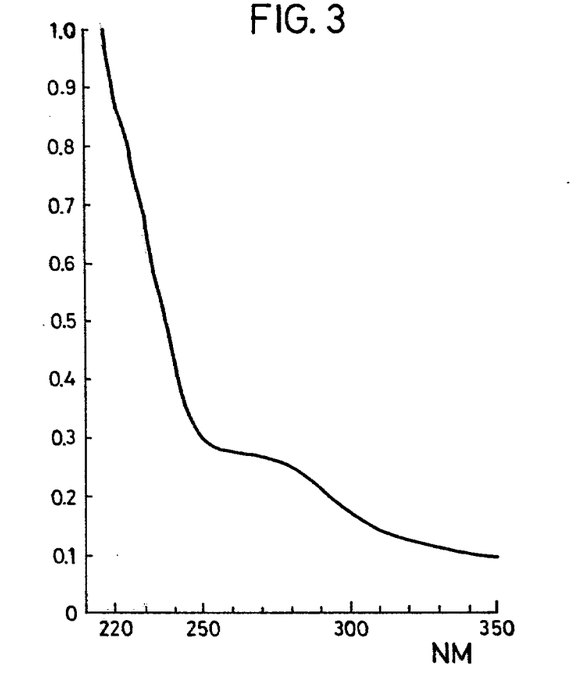
FIG. 3 is an ultraviolet absorption spectrum of the inventive material.

FIG. 3 illustrates the ultraviolet absorption spectrum of the active material of the invention as measured in a 0.1% (W/V) solution of cyclohexane-ethanol mixture (volume ratio of 1:1) with a self-recording spectrophotometer, Hitachi 340 Model.

A favourable embodiment for the method of producing the new surface active material according to the present invention is explained in detailed below:

(a) The lung, which was excised from normal mammal, is divided into fist-sized lumps, which is then, after the unwanted blood vessels, windpipes, fat bodies and blood are removed therefrom, minced finely with meat-grinder or homogenizer. As the mammal, cattle, horses, sheep, pigs, dogs, cats or rabbits are employed suitably. When the minced lung is lyophilized, it is capable of preservation without suffering quality-change or putrefaction.

(b) An electrolyte solution such as physiological saline is added to the minced lung prepared above and the resultant mixture is stirred at 0°–10° C. for 30–120 minutes. The mixture is either filtered under pressure or centrifuged at a low speed of 500–1,500 rpm to take up an extract.

(c) The extract is then centrifuged at a high speed of 12,000–16,000 rpm at 0°–10° C. to obtain "crude sediment". Fragments of said minced lung remained in the "crude sediment" may be removed by re-suspending the "crude sediment" in an electrolyte solution, followed by centrifugation of the suspension at a low speed of 500–1,500 rpm.

(d) "Crude sediment" obtained above is suspended in water and the density of the suspension is adjusted to a value of 1.07–1.20 by dissolving sodium chloride therein. The adjusted suspension is centrifuged at a middling speed of 4,000–10,000 rpm at 0°–10° C. for 20–180 minutes to divide it into three layers, the top emulsified scum layer (hereinafter abbreviated as "top layer") of which is then taken up. The purity (desired surface active material content) of "top layer" may be improved by re-suspending the layer in a 9.3–26.0% (W/V) aqueous solution of sodium chloride followed by centrifugation of the suspension at a middling speed of 4,000–10,000 rpm.

(e) The above "top layer" is suspended in water and the suspention is subjected to dialysis through suitable semipermeable membrane at 4°–10° C. for 12–48 hours, whereby the inorganic salts such as sodium chloride and water-soluble organic compounds of low molecule weight remained in said layer are removed into outer water. As the semipermeable membrane, the cellophane membrane, collodion membrane and bladder membrane may be advantageously used.

(f) The suspension which has remained inside the membrane and which contains the non-dialyzed materials in the above dialysis (hereinafter abbreviated as "non-dialyzed suspension") is centrifuged at a high speed of 12,000–16,000 rpm at 0°–10° C. for 5–30 minutes to take up "pure sediment", the purity of which may be improved further by such a procedure as "pure sediment" re-suspended in an electrolite solution is floated on an aqueous 0.25–0.80 M sucrose solution, followed by centrifugation of the floated suspension at an ultra-high speed of 18,000–40,000 rpm at 0°–6° C. for 1–24 hours. Such a procedure for improvement of the purity as above may be conducted effectively at the previously described step wherein "top layer" or "non-dialyzed suspension" has been taken up. Thus obtained "pure sediment" is then dried under reduced pressure or lyophilized.

(g) One part of the dried "pure sediment" is suspended in 100–300 parts of acetone and, after left at $-10°\sim +10°$ C. for 30–60 minutes, the suspension is filtered to take up an acetone-insoluble material, whereby excessive amounts of neutral lipid and total cholesterol remained in "pure sediment" are selectively removed therefrom. The acetone-insoluble material is dried under reduced pressure and one part of the dried material is suspended in 100–300 parts of organic solvents mixture. The suspension is, after left for 10–20 minutes, filtered to take up "purified filtrate", whereby most of the foreign protein remained in the acetone-insoluble material are selectively removed. As said organic solvents mixture is desirably employed the mixture of chloroform-methanol (2:1) (volume ratio; hereinafter the same), chloroform-ethanol (2:1), chloroform-isopropanol (1:1) or ethyl ether-ethanol (1:3). "Purified filtrate" taken up above was subjected to the sterility test prescribed in the Pharmacopoeia of Japan, 9th revised edition, B p232, to confirm its sterility, so the subsequent procedures were conducted under sterile conditions.

(h) "Purified filtrate" is mixed with sterile water and after left for 1–24 hour(s), the mixture is subjected to filtration, the filtrate of which is then concentrated under reduced pressure to obtain a solid residue. The solid residue has generally the same chemical composition as that of the surface active material of the present invention as described previously, so the residue may be lyophilized to produce finally the desired material. In case of the phospholipid content based on said solid residue being however less than 75.0%, such case occuring occasionally, the same lipid is advantageously added to make the phospholipid content 75.0–95.5%. As the phospholipid to be added, phosphatidylglycerol, phosphatidylcholine having two saturated fatty acid residues (e.g., dipalmitoylphosphatidylcholine) or mixture thereof is suitably used.

The chemical composition, physicochemical properties and physiological properties (including toxicity, intra-alveolar surface tension-reducing capacity and clinical effect) of the surface active material of the invention produced in the above are particularly explained below.

[I] Chemical composition

The active material contains phospholipid, neutral lipid, total cholesterol, carbohydrate and protein, all derived from the lung tissue of mammals. In Table I are shown the contents (%) of these components based on the whole active material; the ratio of phospholipid content to protein content; the individual phospholipid contents (%) based on the total phospholipid; and the content (%) of phosphatidylcholine having two saturated fatty acid residues based on the total phosphatidylcholine. Besides, the ratio of phospholipid content to protein content and the content (%) of phosphatidylcholine having two saturated fatty acid residues based on the total phosphatidylcholine both calculated from the values described in the literature are also added to Table I for the sake of comparison.

In the above, the estimations of individual component contents were conducted in the following manners. The phospholipid content was estimated by determining its phosphorous content according to the method of King et al., followed by multiplying the determined value by 25. The neutral lipid content was estimated according to the acetylacetone colorimetric method but calculating it in glycerol trioleate equivalent. The total cholesterol content was estimated according to the Rosenthal's method but calculating it in cholesterol equivalent, and the carbohydrate content was estimated according to the phenol-sulfuric acid method but calculating it in glucose equivalent, while the protein content was estimated according to the method of Lowry et al. but calculating it in bovine serum albumin equivalent. The water content was estimated by th Karl Fischer's method (cf. Biochemical Journal, 26, 292, 1932; Clinica Chimica Acta, 22, 393, 1968; Journal of Laboratory and Clinical Medicine, 50, 318, 1957; Analytical Chemistry, 28, 350, 1956; and Journal of Biological Chemistry, 193, 265, 1956).

The individual phospholipid contents were estimated in such a way as the whole phospholipid was subjected to fractionation by two-dimensional thin-layer chromatography with a thin layer of silica gel 60 (0.25 mm in thickness, 20×20 cm in size; mfd. by Merck Co.) employing the first dimensional developing solvent of chloroform-methanol-water mixture (volume ratio of 65:25:4), the second dimensional developing solvent of chloroform-methanol-7 N aqueous ammonia solution mixture (volume ratio of 230:90:15) and the color developer of iodine, followed by estimation of the phospholipid contents in respective thin layer fractions by using the same estimating method of the phospholipid content as described previously. The content of phosphatidylcholine having two saturated fatty acid residues was estimated in such a manner as the whole phosphatidylcholine was subjected to fractionation by the method of Shimojo et al. (cf. Journal of Lipid Research, 15, 525, 1974), followed by estimation of the phosphatidylcholine content in the thin layer fraction containing the phosphatidylcholine having two saturated fatty acid residues by using the same estimating method of the phospholipid content as described previously.

TABLE I

|  | Surface active material of the invention | Conventional pulmonary surfactant |
|---|---|---|
| Composition of the material |  |  |
| Phospholipid | 75.0–95.5% |  |
| Neutral lipid | 1.8–14.0% |  |
| Total cholesterol | 0.0–3.0% |  |
| Carbohydrate | 0.1–1.5% |  |
| Protein | 0.5–5.0% |  |
| Water | 1.7–6.0% |  |
| Ratio of phospholipid content to protein content | 15.0 or greater | 2.8–6.0 |
| Composition of phospholipid |  |  |
| Phosphatidylcholine | 63.0–85.5% |  |
| Phosphatidylglycerol | 3.0–12.0% |  |
| Phosphatidylethanolamine | 2.5–7.7% |  |
| Sphingomyelin | 5.7–7.0% |  |
| Phosphatidylinositol and Phosphatidylserine | 2.4–7.4% |  |
| Lysophosphatidylcholine | 0.5–2.1% |  |
| Others | not greater than 1.0% |  |
| Content of phosphatidylcholine having two saturated fatty acid residues based on the total phosphatidylcholine | 67.5–90.3% | 44.5–59.1% |

As is evident from the data shown in Table I, the surface active material of the present invention has the characteristics of a low content of protein and a high content of phosphatidylcholine having two saturated fatty acid residues, the fatty acid of said phosphatidylcholine being predominantly palmitic acid.

[II] Physicochemical properties (a) Surface tension-reducing capacity

According to Wilhelmy's method, the present active material was added dropwise to the surface of physiological saline in an amount of 0.3–0.8 μg per square centimeter of surface area at a temperature of 15°–25° C., and the minimum surface tension range of 2.1–8.6 dynes/cm and the maximum surface tension range of 48.2–58.0 dynes/cm were obtained (cf. FIG. 1). These values indicate that the surface tension of physiological saline when the present material has been added is approximately 1/34.3–1/1.2 times as little as that of physiological saline in control test. The stability index (cf. Archives of Environmental Health, 2, 280, 1961) of the material was 1.40–1.86, while the area bounded by the hysteresis curve thereof was 52±3.2 cm². The compressibility at 15 dynes/cm which was expressed by the slope constant at point A in FIG. 1 was 0.002–0.033.

(b) Optical activity

The specific rotatory power of the present material was estimated by using automatic polarimeter, DIP-180 (mfd. by Nihon Bunkō Co., Ltd.), and was found $[\alpha]_D^{26}$: $+1.0 \sim +8.1$ (C 0.2, benzene).

(c) Solubility 10 mg each of the material was added to 10 ml of individual solvent and the resulting mixture was stirred for approximately 10 seconds. The solubility was, as shown in Table II, expressed as positive (+) when dissolved optically, or as negative (−) when did not dissolve optically. Besides, aqueous suspensions of the material were found to be neutral or weakly acidic.

TABLE II

| Solvent | Volume ratio | Solubility |
|---|---|---|
| Chloroform |  | + |
| Benzene |  | + |
| Water |  | − |
| Methanol |  | − |
| Ethanol |  | − |
| Acetone |  | − |
| Cyclohexane-ethanol | 1:1 | + |
| Ethyl ether-methanol | 1:1 | + |
| Petroleum ether-ethanol | 1:1 | + |
| Acetone-methanol | 1:1 | − |
| Chloroform-methanol | 2:1 | + |

(d) Absorption spectra

The infrared and ultraviolet absorption spectra of the material were as those illustrated in FIGS. 2 and 3, respectively.

[III] Toxicity (a) Acute toxicity test

The present material was respectively administered orally and intraperitoneally to male ICR mice and male Wistar rats, both 5-weeks old, and were found, for mice, the oral $LD_{50}$ of not less than 3 g/kg and the intraperitoneal $LD_{50}$ of not less than 2 g/kg, while for rats, the oral $LD_{50}$ of not less than 4 g/kg and the intraperitoneal $LD_{50}$ of not less than 2.5 g/kg.

(b) Subacute toxicity test

The material was administered intraperitoneally to mature Wistar rats in a daily dose of 500 mg/kg of body weight for a period of one month. However, any changes in body weight did not occur and any abnormal findings in the optical and histological observations of the lungs as well as other principal organs were not noted. Moreover, no systemic abnormalities due to foreign proteins were observed.

[IV] Intra-alveolar surface tension-reducing effect (a) Test for alveolar volume-maintaining capacity Using 7 rabbit fetuses removed after 27 days of gestation, the alveolar volume-maintaining capacity of the material was tested at gradually decreasing endotracheal pressures. That is, the neck of each fetus was incised to expose the trachea, to which a water manometer was then connected directly, and, beginning at 5 minutes after the treatment with the material, the alveolar volume and the endotracheal pressure thereof were continuously measured with said manometer. Adjustment of the endotracheal pressure was conducted by employing an independently-acting 2-channel syringe pump No. 940 (mfd. by Harvard Inc.) connected directly to the trachea. The treatment with the material was carried out by instilling 0.4-0.5 ml of 1.0-1.5% (W/V) suspension of the material in physiological saline into the trachea. The alveolar volume was expressed as the value per kilogram of body weight, and the alveolar volume in the control group consisting of 7 fetuses were measured in the same manner as the above except using only physiological saline in place of the suspension of the material. The results of test are shown in Table III.

TABLE III

| Endotracheal pressure ($cmH_2O$) | Alveolar volume (ml/kg) | |
|---|---|---|
| | Treatment group with the material | Control group |
| 30 | 55 ± 2 | 13 ± 2 |
| 25 | 49 ± 3 | 9 ± 3 |
| 20 | 47 ± 3 | 8 ± 3 |
| 15 | 44 ± 3 | 6 ± 2 |
| 10 | 39 ± 4 | 4 ± 2 |
| 5 | 25 ± 3 | 2 ± 2 |
| 0 | 17 ± 4 | 0 |

It is evident from the data shown in Table III that at an endotracheal pressure of 30 $cmH_2O$, the alveolar volume of the treatment group is not less than 4.2 times as large as that of the control group. Even at an extremely low endotracheal pressure of 5 $cmH_2O$, the alveolar volume of the treatment group is as large as about 25 ml/kg, while that of the control group is very small.

(b) Test for intra-alveolar pressure-reducing capacity

Using 5 rabbit fetuses removed after 27 days of gestation, the endotracheal pressure required for maintaining the ventilation volume per respiration at 10 ml/kg of body weight under artificial respiration was measured by using the respirometer MFP-1100 (mfd. by Nihon Koden Co., Ltd.). The measurement was conducted 5 minutes after instilling 0.4 ml of 1.0% (W/V) supension of the material in physiological saline into the trachea. The endotracheal pressure in the control group consisting of 5 fetuses was measured in the same manner as the above except using only physiological saline in place of the suspension of the material.

From the result of the above test, it was revealed that a low pressure of approximately 12 $cmH_2O$ on the average was sufficient for the treatment group, while for the control group was required a high pressure of 45 $cmH_2O$ which corresponded to approximately 4 times that of the former.

[V] Clinical test 5 newborn infants with severe HMD the gestational age of which were 28-32 weeks were treated with the present material once or twice, and after a period of 6 months, the fate of the infants and the presence or absence of lung disorders thereof were observed. Treatment with the material was conducted by instilling a 1% (W/V) suspension of the material in physiological saline directly into the tracheas so that the material per kilogram of body weight in each treatment amounts to 100 mg, and simultaneously the conventional continuous possitive airway pressure method described previously was applied thereto. The results of test are shown in Table IV, "severity of HMD" described in which was judged from chest radiographic findings expressed with five grades on the criteria by Matsumura et al. (cf. Shonika, 15, 89, 1974), while "time of treatment" in which refers to the time from the birth theretofore.

TABLE IV

| Case | | Time of treatment (hours) | | Outcomes | |
|---|---|---|---|---|---|
| No. | Body weight (kg) | Severity of HMD | 1st | 2nd | Fate | Lung disorders |
| 1 | 1.4 | V | 13 | 65 | Survived | None |
| 2 | 1.1 | III | 7 | 68 | Survived | None |
| 3 | 1.1 | V | 4 | | Survived | None |
| 4 | 1.8 | V | 15 | | Survived | None |
| 5 | 1.4 | V | 6 | 14 | Survived | None |

From the above Table IV, it is demonstrated that even the newborn infants of short gestation period with severe HMD have been cured by the treatment with the surface active material of the present invention. In contrast, it has been known that according to the conventional treatment methods, all newborn infants with HMD of severity V died within 72 hours after birth.

The chemical composition, physicochemical properties any physiological properties of the surface active material of the present invention as described particularly in the above reveal that the present material is a novel material having useful medicinal effects and a high degree of safety.

Thus, pharmaceutical composition containing the active material of the invention is regarded as useful remedy for HMD. The pharmaceutical composition of the present invention is employed at such a dose per treatment as it contains, e.g., for newborn infants with HMD, 50-400 mg, desirably 100-200 mg, of the surface active material of the present invention. The composition is generally suspended in 5-20 ml, desirably 6-10 ml, of a suitable solvent medium and the suspension is instilled directly into the trachea of the patient within 72 hours after his birth. The number of treatments is generally one or two, however it may be three or more times, if necessary. Said dose and treatment method may be modified in consideration of the condition of the patient as well as the concomitantly used other drugs and/or treatment methods.

Where the pharmaceutical composition of the present invention is made into suspension form, may be added thereto suitable additives for the sake of enhancing the dispersion and stability of the active material. Where the pharmaceutical composition is made into liquid form, stabilizers, preservatives, osmotic pressure regulators, buffering agents and suspending agents of the liquid may be added thereto. If desired, suitable germicides may also be used as an additive. Where the composition is made into powder which is intended to use in the form of suspension in a solvent when used, suitable excipiens, binders and the like can be added thereto besides the aforesaid additives. Suitable suspension media include water and electrolyte solutions such as physiological saline.

The pharmaceutical composition of the present invention may be charged in hermetically sealed containers such as vials and ampules and preserved sterilely.

Method for preparing the pharmaceutical composition of the present invention is exemplified below:

PHARMACEUTICAL COMPOSITION 1

100 mg of the active material of the invention and 6 ml of physiological saline were charged into a 10 ml-vial under sterile conditions and the vial was sealed with a metal-clamped rubber stopper to prepare a pharmaceutical composition of suspension form.

PHARMACEUTICAL COMPOSITION 2

7,500 mg of the active material was added to 520 ml of distilled water and the mixture was stirred by an ultrasonic generator to form an uniform suspension. 10 ml each of the suspension was charged into fifty individual 30 ml-vials under sterile conditions and lyophilized, followed by sealing the vials with a metal-clamped rubber stopper under sterile conditions. Each vial was accompanied by 9 ml of sterile physiological saline in order to prepare a suspension therewith when used.

PHARMACEUTICAL COMPOSITION 3

150 mg of the active material and 50 mg of glucose were charged into a 10 ml-ampule according to the routine powder filling technique, and the ampule was sealed under sterile conditions. The ampule was accompanied by 10 ml of sterile physiological saline in order to prepare a suspension therewith when used.

The invention will now be illustrated by the following examples; however the descriptions in these examples are not to be considered as limitations, since many changes in the details may be made without departing from the spirit of the invention.

EXAMPLE 1

32.0 kg of lungs excised from ten cattle was washed with water to remove uncoagulated or coagulated blood and the like, all adhering thereto. These lungs were divided into fist-sized lumps, freed of unnecessary blood vessels, windpipes and fat bodies by using knives, scissors or the like, and washed again with water. The lumps were finely minced by a meat-grinder and then lyophilized to prepare dried minced lung (4.6 kg).

520 g taken out of the dried minced lung prepared above was added to 18.0 lit. of physiological saline and the mixture was stirred at 4° C. for 30 minutes. The mixture was filtered with a hydraulic press under a pressure of approximately 100 kg/cm$^2$ to obtain an extract (16.2 lit.). While being injected into a centrifuge at a flow rate of 6.2 lit. per hour, the extract was continuously centrifuged at a high speed of 14,000 rpm at 5° C. to take up a "crude sediment", which was then suspended in 980 ml of physiological saline with a homogenizer. The suspension was centrifuged at a low speed of 1,000 rpm at 4° C. to remove any sediment of residual fragments of lung tissue and the like therefrom. To the upper layer suspension (880 ml) taken up in the above centrifugation was added 230 g of sodium chloride so as to adjust its density to approximately 1.20, and the adjusted suspension was centrifuged at a middling speed of 5,000 rpm at 4° C. for 30 minutes to take up a "top layer". "Top layer" was re-suspended in 400 ml of a 26% (W/V) aqueous sodium chloride solution and then centrifuged at a middling speed of 5,000 rpm at 4° C. for 30 minutes, whereby the purity of "top layer" was improved. The purified "top layer" was suspended in distilled water and the suspension was subjected to dialysis with a cellophane membrane to remove the contained inorganic salts into outer distilled water. "Non-dialyzed suspension" was taken up and centrifuged at a high speed of 14,000 rpm at 40° C. for 20 minutes to obtain a "pure sediment", which was then lyophilized (yield of 5.2 g). The dried "pure sediment" was suspended in 1.2 lit. of acetone at 6° C. and, after left for 60 minutes, the suspension was filtered through filter paper to take up an acetone-insoluble material. The acetone-insoluble material was dried under reduced pressure at room temperature and then suspended in 1 lit. of chloroform-methanol mixture (volume ratio of 2:1). The resulting suspension was left for 10 minutes and then filtered through a glass filter to take up a "purified filtrate". A sample taken out of "purified filtrate" was subjected to sterility test to find its sterility. (The subsequent procedures were carried out under sterile conditions; hereinafter the same.) The above "purified filtrate" was washed by mixing with 170 ml of sterile water at 6° C. followed by leaving the resultant mixture overnight. The organic solvent layer was taken up and concentrated under reduced pressure to obtain a solid residue (3.4 g). A sample taken out of the solid residue was lyophilized and then analyzed, and the phospholipid content based thereon was found to be 71.0%. Accordingly, 1.6 g of dipalmitoylphosphatidylcholine and 0.3 g of phosphatidylglycerol were added to the remainder of the residue, and the mixture was suspended to distilled water and then lyophilized to produce a white powder of the surface active material of the invention (5.2 g). The chemical composition of the present active material is arranged in Table V described hereinafter (the same for all the subsequent Examples).

EXAMPLE 2

800 g taken out of the dried minced lung prepared in Example 1 was added to 34.0 lit. of physiological saline and the mixture was stirred at 8° C. for 1.5 hours. While being injected into a centrifuge at a flow rate of 8.1 lit. per hour, the mixture was continuously centrifuged at a low speed of 1,000 rpm at 8° C. to take up an extract (30.0 lit.). Then, while being injected into a centrifuge similarly at a flow rate of 4.7 lit. per hour, the extract was continuously centrifuged at a high speed of 16,000 rpm at 2° C. to obtain a "crude sediment", which was then mixed with 1.2 lit. of water and suspended therein with a homogenizer. To the resulting suspension was added 250 g of sodium chloride so as to adjust its density to approximately 1.15, and the suspension was centrifuged at a middling speed of 4,000 rpm at 6° C. for 150 minutes to take up a "top layer". This "top layer" was suspended in distilled water and the suspension was subjected to dialysis with a cellophane membrane to remove the contained inorganic salts into outer distilled water. "Non-dialyzed suspension" taken up was floated on a 0.70 M aqueous sucrose solution and centrifuged at an ultra-high speed of 20,500 rpm at 4° C. for 90 minutes. The milky layer formed at the boundary between the aqueous sucrose solution layer and "top layer" was taken up and subjected to dialysis again with a cellophane membrane to remove the contained sucrose into outer distilled water. "Non-dialyzed suspension" was then centrifuged at a high speed of 12,000 rpm at 2° C. for 15 minutes to obtain a "pure sediment", which was then lyophilized (yield of 7.3 g). The dried "pure sediment" was suspended in 1.0 lit. of acetone at −10° C., and after left for 30 minutes, the suspension was filtered through a glass filter to take up an acetone-insoluble material. The acetone-insoluble material was dried under reduced pressure at 20° C. and then suspended in 1.5 lit. of chloroform-ethanol mixture (volume ratio of 2:1). The resulting suspension was left for 10 minutes and then filtered through a glass filter to take up a "purified filtrate". "Purified filtrate" was washed by mixing with 300 ml of sterile distilled water followed by leaving the resultant mixture at 4° C. for 3 hours. The organic solvent layer was taken up and concentrated under reduced pressure, then lyophilized to produce a sterile white powder of the surface active material of the invention (4.8 g).

EXAMPLE 3

80 g of the dried minced lung prepared in Example 1 was added to 2.8 lit. of physiological saline and the mixture was stirred at 0° C. for 2 hours. The mixture was filtered with gauze by gravity, and the gauze was squeezed to obtain an extract (2.3 lit.). The extract was centrifuged at a speed of 1,500 rpm at 8° C. for 10 minutes to remove any sediment of residual fragments of lung tissue and the like. The upper layer suspension taken up in the above was centrifuged again but at a speed of 12,000 rpm at 0° C. for 20 minutes to obtain a "crude sediment", which was then suspended in 130 ml of physiological saline with a homogenizer. To the resulting suspension was added 8.1 g of sodium chloride to adjust its density to approximately 1.07, and the adjusted suspension was centrifuged at a speed of 10,000 rpm at 0° C. for 180 minutes to take up a "top layer". This "top layer" was re-suspended in 130 ml of a 14.0% (W/V) aqueous sodium chloride solution and then centrifuged at a speed of 5,000 rpm at 0° C. for 90 minutes, whereby the purity of "top layer" was improved. Such purification procedure was repeated twice. The purified "top layer" was suspended in distilled water and the suspension was subjected to dialysis with a cellophane membrane to remove the inorganic salts into outer distilled water. "Non-dialyzed suspension" was centrifuged at a speed of 16,000 rpm at 6° C. for 5 minutes to take up a "pure sediment", which was then lyophilized (yield of 930 mg). The dried "pure sediment" was suspended in 270 ml of acetone at 0° C. and, after left for 40 minutes, the suspension was filtered through a glass filter to take up an acetone-insoluble material. The acetone-insoluble material was dried under reduced pressure and then suspended in 210 ml of ethyl ether-ethanol mixture (volum ratio of 1:3). The resulting suspension was left for 15 minutes and then filtered through a glass filter to take up a "purified filtrate". The above "purified filtrate" was concentrated under reduced pressure to obtain a concentrate. The phospholipid content of the concentrate was found to be 73.0%. Accordingly, 410 mg of dipalmitoylphosphatidylcholine and 120 mg of phosphatidylglycerol were added to the concentrate, and the mixture was suspended in distilled water and then lyophilized, whereby a sterile white powder of the surface active material of the invention (1,071 mg) was produced.

EXAMPLE 4

30 g of the dried minced lung prepared in Example 1 was added to 1.3 lit. of physiological saline and the mixture was stirred at 2° C. for an hour. The mixture was filtered with gauze, which was then squeezed by hand to obtain an extract (1.1 lit.). The extract was centrifuged at a speed of 15,000 rpm at 4° C. for 15 minutes to take up a "crude sediment", which was then suspended in 60 ml of physiological saline with a homogenizer. The suspension was centrifuged at a speed of 1,500 rpm at room temperature for 10 minutes to remove any sediment of residual fragments of lung tissue and the like. To 56 ml of the upper layer suspension taken up in the above was added 14 g of sodium chloride to adjust its density to approximately 1.20, and the suspension was centrifuged at a speed of 6,000 rpm at 4° C. for 60 minutes to take up a "top layer". The purity of "top layer" was improved by re-suspending the layer in 60 ml of a 25.0% (W/V) aqueous sodium chloride solution followed by centrifugation of the resulting suspension at a speed of 6,000 rpm at 4° C. for 60 minutes to take up "top layer" thereof again. Such purification procedure was repeated three times. The purified "top layer" was suspended in distilled water and then subjected to dialysis with a cellophane membrane to remove the contained inorganic salt into outer distilled water. "Non-dialyzed suspension" was centrifuged at a speed of 15,000 rpm at 2° C. for 15 minutes to take up a "pure sediment", which was then lyophilized (yield of 302 mg). The dried "pure sediment" was suspended in 60 ml of acetone at 2° C., and the suspension was, after left for 30 minutes, filtered through a glass filter to take up an acetone-insoluble material. The acetone-insoluble material was dried under reduced pressure and then suspended in 50 ml of chloroform-methanol mixture (volume ratio of 2:1). The resulting suspension was, after left for 15 minutes, filtered through a glass filter to take up a "purified filtrate", which was then concentrated under reduced pressure to obtain a solid residue. The phospholipid content of the residue was found to be 71.0%. Accordingly, 150 mg of dipalmitoylphosphatidylcholine and 34 mg of phosphatidylglycerol were added to the residue, and the mixture was suspended in sterile distilled water followed by lyophilization of the suspension to produce a sterile white powder of the surface active material of the invention (357 mg).

EXAMPLE 5

4.5 kg of lung excised from a horse was processed in the same manner as described in Example 1 to prepare the dried minced lung (750 g). Using 30 g taken out of the dried minced lung, the same subsequent procedures as described in Example 4 were conducted to obtain a solid residue. The phospholipid content of the residue was found to be 68.5%. To the residue were added 280 mg of dipalmitoylphosphatidylcholine and 28 mg of phosphatidylglycerol, and the mixture was suspended in distilled water with the aid of an ultrasonic generator. The resulting suspension was lyophilized to produce a sterile white powder of the surface active material of the invention (448 mg).

EXAMPLE 6

1.1 kg of lungs excised from two sheep was processed in the same manner as described in Example 1 to prepare the dried minced lung (147 g). Using 30 g taken out of the dried minced lung, the same subsequent procedures as described in Example 4 were conducted to obtain a solid residue. The phospholipid content of the residue was found to be 70.6%. To the residue were added 149 mg of dipalmitoylphosphatidylcholine and 21 mg of phosphatidylglycerol, and the mixture was suspended in distilled water with an ultrasonic generator. The resulting suspension was lyophilized to produce a sterile white powder of the active material of the invention (314 mg).

EXAMPLE 7

2.7 kg of lung excised from a pig was processed in the same manner as described in Example 1 to prepare the dried minced lung (385 g). Using 30 g taken out of the dried minced lung, the same subsequent procedures as described in Example 4 were conducted to obtain a solid residue. The phospholipid content of the residue was found to be 69.4%. To the residue were added 207 mg of dipalmitoylphosphatidylcholine and 34 mg of phosphatidylglycerol, and the mixture was suspended in distilled water with an ultrasonic generator. The resulting suspension was lyophilized to produce a sterile white powder of the active material of the invention (365 mg).

EXAMPLE 8

330 g of lung excised from a mongrel dog was processed in the same manner as described in Example 1 to prepare the dried minced lung (37 g). Using 30 g taken out of the dried minced lung, the same subsequent procedures as described in Example 4 were conducted to obtain a solid residue. The phospholipid content of the residue was found to be 63.3%. To the residue were added 174 mg of dipalmitoylphosphatidylcholine and 28 mg of phosphatidylglycerol, and the mixture was suspended in distilled water. The resulting suspension was lyophilized to produce a sterile pale-yellow powder of the active material of the invention (370 mg).

EXAMPLE 9

3.0 kg of lung excised from a cattle was processed in the same manner as described in Example 1 to prepare the minced lung (2.6 kg). The minced lung was added to 15.0 lit. of physiological saline and the mixture was stirred at 10° C. for an hour, followed by press-filtration with a hydraulic press under a pressure of approximately 120 kg/cm$^2$ to obtain an extract. The filtration residue was mixed with 2.0 lit. of physiological saline and press-filtered again to obtain a second extract. The total volume of the above two extracts was 15.3 lit. While being injected into a centrifuge at a flow rate of 3.5 lit. per hour, the extract was continuously centrifuged at a high speed of 15,000 rpm at 6° C. to take up a "crude sediment", which was then suspended in 1,500 ml of physiological saline with a homogenizer. The resulting suspension was centrifuged at a low speed of 1,500 rpm at room temperature for 10 minutes to remove out any sediment of residual fragments of lung tissue. To 1,350 ml of the upper layer suspension taken up in the above was added 230 g of sodium chloride to adjust its density to approximately 1.13, and the suspension was centrifuged at a middling speed of 4,000 rpm at 10° C. for 120 minutes to take up a "top layer". The purity of "top layer" was improved by re-suspending the layer in 900 ml of a 25.0% (W/V) aqueous sodium chloride solution followed by centrifugation of the resulting suspension at a middling speed of 5,000 rpm at 8° C. for 60 minutes. The purified "top layer" was suspended in distilled water and the suspension was desalted by subjecting it to dialysis with a cellophane membrane against outer distilled water. "Non-dialyzed suspension" was centrifuged at a high speed of 13,000 rpm at 3° C. for 15 minutes to take up a "pure sediment", which was then lyophilized (yield of 3.9 g). The dried "pure sediment" was suspended in 780 ml of acetone at 0° C., and suspension was, after left for 45 minutes, filtered through a glass filter to take up an acetone-insoluble material. The acetone-insoluble material was dried under reduced pressure at 10° C. and then suspended in 800 ml of chloroform-isopropanol mixture (volume ratio of 1:1). The resulting suspension was left for 10 minutes and then filtered through a glass filter to obtain a "purified filtrate". "Purified filtrate" was, after washed by mixing 150 ml of sterile distilled water thereto followed by leaving the mixture at 0° C. for 12 hours, concentrated under reduced pressure and then lyophilized to produce a sterile white powder of the surface active material of the invention (2.7 g).

EXAMPLE 10

4.4 kg of lung excised from a horse was processed in the same manner as described in Example 1 to prepare the minced lung (3.9 kg). The minced lung was treated in the same subsequent manners as described in Example 9 to produce a sterile white powder of the surface active material of the invention (3.4 g).

EXAMPLE 11

120 g of the dried minced lung prepared in Example 1 was added to 4.0 lit. of physiological saline and the mixture was stirred at 5° C. for 2 hours. While being injected into a centrifuge at a flow rate of 7.5 lit. per hour, the mixture was centrifuged at a low speed of 1,200 rpm at 5° C. to take up an extract (3.5 lit.). The extract was centrifuged again but at a high speed of 14,000 rpm at 6° C. for 30 minutes to take up a "crude sediment", which was then suspended in 150 ml of water with a homogenizer. To the resulting suspension was added sodium chloride to adjust its density to approximately 1.17, and the suspension was centrifuged at a middling speed of 6,000 rpm for 60 minutes. "Top layer" taken up in the above centrifugation was floated on an aqueous sucrose solution having gradient concentration of 0.25–0.80 M and then centrifuged at an ultra-high speed of 22,000 rpm at 4° C. for 120 minutes to take up the milky layer suspension. Said milky layer suspension was suspended in distilled water and then subjected to dialysis with a cellophane membrane to remove the contained sucrose, salts and the like into outer distilled water. "Non-dialyzed suspension" was centrifuged at a high speed of 12,000 rpm at 2° C. for 15 minutes to take up a "pure sediment", which was then lyophilized (yield of 1.1 g). The dried "pure sediment" was suspended in 200 ml of acetone at 0° C., and the suspension was, after left for 30 minutes, filtered through a glass filter to take up an acetone-insoluble material. The acetone-insoluble material was dried under reduced pressure at room temperature and then suspended in 150 ml of chloroform-ethanol mixture (volume ratio of 2:1). The resulting suspension was left for 10 minutes and then filtered by suction through a glass filter to take up a "purified filtrate". The above "purified filtrate" was washed by mixing 400 ml of sterile water thereto followed by leaving the mixture at 4° C. for 6 hours, and then concentrated under reduced pressure to obtain a solid residue. The solid residue was suspended in sterile distilled water and the suspension was lyophilized to produce a sterile white powder of the active material of the invention (530 mg).

EXAMPLE 12

The same procedures as described in Example 11 were conducted and 150 ml of the adjusted suspension of "crude sediment" having a density of approximately 1.17 was prepared. The suspension was centrifuged at a middling speed of 5,000 rpm for 90 minutes to take up a "top layer". "Top layer" was suspended in distilled water and the suspension was desalted by subjecting it to dialysis with a cellophane membrane against outer distilled water. "Non-dialyzed suspension" was centrifuged at a speed of 14,000 rpm at 2° C. to take up a "pure sediment". "Pure sediment" was re-suspended in distilled water and the suspension was floated on a 0.55 M aqueous sucrose solution, followed by centrifugation thereof at an ultra-high speed of 28,000 rpm at 2° C. for 90 minutes to take up the milky layer formed at the boundary between the aqueous sucrose solution layer and "top layer". The milky layer was treated in the same subsequent procedures as described in Example 11 to produce a sterile white powder of the active material of the invention (470 mg).

EXAMPLE 13

35 kg of lungs excised from ten cattle was processed in the same manner as described in Example 1 to prepare the dried minced lung (5.1 kg). 5.0 kg of the dried minced lung was added to 200 lit. of physiological saline and the mixture was, after stirred at 10° C. for 80 minutes, divided into approximately equal five portions, each of which was pressfiltered by using a hydraulic press under a pressure of approximately 110 kg/cm$^2$ to obtain an extract. The total volume of the extracts was 186 lit. While being injected into a centrifuge at a flow rate of 10 lit. per hour, the combined extract was continuously centrifuged at a high speed of 15,000 rpm at 2° C. to take up a "crude sediment", which was then suspended in 12.0 lit. of physiological saline with an ultrasonic generator. The resulting suspension was continuously centrifuged at a low speed of 1,500 rpm at 2° C. To the upper layer suspension (10.8 lit.) taken up in the above was added sodium chloride to adjust its density to approximately 1.20. The suspension was centrifuged at a middling speed of 7,500 rpm at 4° C. for 60 minutes to take up a "top layer," the purity of which was then improved by re-suspending the layer in 5.0 lit. of a 26.0% (W/V) aqueous sodium chloride solution followed by centrifugation of the resulting suspension at a middling speed of 7,500 rpm at 4° C. for 60 minutes. The purified "top layer" was suspended in distilled water and the suspension was subjected to dialysis with a cellophane membrane against outer distilled water. "Non-dialyzed suspension" was centrifuged at a speed of 12,000 rpm at 2° C. for 30 minutes to take up a "pure sediment", which was then lyophilized (yield of 47.6 g).

The dried "pure sediment" was suspended in 10.0 lit. of acetone at 10° C., and the suspension was, after left for 60 minutes, filtered by suction through a glass filter to take up an acetone-insoluble material. The acetone-insoluble material was dried under reduced pressure at room temperature and then suspended in 8.5 lit. of chloroform-methanol mixture (volume ratio of 2:1). The suspension was left for 10 minutes and then filtered by suction through a glass filter to take up a "purified filtrate". The above "purified filtrate" was washed by mixing 1.5 lit. of sterile distilled water thereto followed by leaving the resulting mixture at 5° C. for 24 hours. Thereafter, "purified filtrate" was concentrated under reduced pressure to obtain a solid residue (38.4 g). 30.0 g taken out of the solid residue was re-suspended in sterile distilled water with an ultrasonic generator and then lyophilized to produce a sterile white powder of the active material of the invention (28.7 g).

EXAMPLE 14

450 g of the dried minced lung prepared in Example 1 was added to 16.0 lit. of physiological saline and the mixture was stirred for 2 hours. While being injected into a centrifuge at a flow rate of 5.0 lit. per hour, the mixture was centrifuged at a low speed of 1,200 rpm to obtain an extract (13.5 lit.). Then, while being injected into a centrifuge similarly at a flow rate of 5.0 lit. per hour, the extract was centrifuged at a high speed of 15,000 rpm to take up a "crude sediment", which was then suspended in 700 ml of water with an ultrasonic generator. To the resulting suspension was added sodium chloride to adjust its density to approximately 1.20, and the suspension was centrifuged at a middling speed of 7,000 rpm at 2° C. for 50 minutes to take up a "top layer", the purity of which was then improved by re-suspending the layer in 0.7 lit. of a 26.0% (W/V) aqueous sodium chloride solution followed by centrifugation of the resulting suspension at a speed of 7,000 rpm at 2° C. for 50 minutes. The purification procedure was repeated four times. The purified "top layer" was suspended in distilled water and then subjected to dialysis with a cellophane membrane against outer distilled water. "Non-dialyzed suspension" was centrifuged at a speed of 15,000 rpm at 4° C. for 10 minutes to take up a "pure sediment", which was then lyophilized (yield of 4.3 g). The dried "pure sediment" was suspended in 1.3 lit. of acetone at 0° C., and the suspension was, after left for 30 minutes, filtered through a glass filter to take up an acetone-insoluble material. The acetone-insoluble material was dried under reduced pressure at 10° C. and then suspended in 1.1 lit. of chloroform-ethanol mixture (volume ratio of 2:1). The resulting suspension was left for 15 minutes and then filtered through a glass filter to take up a "purified filtrate". The above "purified filtrate" was concentrated under reduced pressure to obtain a solid residue (2.7 g). Since the phospholipid content of the residue was found to be 74.0%, 75 mg of phosphatidylglycerol was added to 1,000 mg of the solid residue, and the resulting mixture was suspended in sterile distilled water followed by lyophilization of the suspension to produce a white powder of the active material of the invention (949 mg).

EXAMPLE 15

100 g of the dried minced lung prepared in Example 1 was added to 4.0 lit. of physiological saline and the mixture was stirred at 6° C. for an hour. The mixture was centrifuged at a low speed of 1,000 rpm at 4° C. to take up an extract (3.6 lit.). Then, the extract was centrifuged at a high speed of 15,000 rpm at 2° C. for 15 minutes to obtain a "crude sediment", which was then suspended in 120 ml of water with a homogenizer. To the resulting suspension was added sodium chloride to adjust its density to approximately 1.15, and the suspension was centrifuged at a middling speed of 8,000 rpm for 80 minutes to take up a "top layer". The purity of "top layer" was improved by re-suspending the layer in 110 ml of a 20.0% (W/V) aqueous sodium chloride solution followed by centrifugation of the suspension at a speed of 6,000 rpm at 0° C. for 80 minutes. The purified "top layer" was suspended in distilled water and the suspension was subjected to dialysis with a cellophane membrane against outer distilled water. "Non-dialyzed suspension" was centrifuged at a speed of 14,000 rpm at 3° C. for 15 minutes to take up a "pure sediment", which was then lyophilized (yield of 1.1 g). The dried "pure sediment" was suspended in 300 ml of acetone at 0° C., and the suspension was, after left for 30 minutes, filtered through a glass filter to take up an acetone-insoluble material. The acetone-insoluble material was dried under reduced pressure at room temperature and then suspended in 200 ml of ethyl ether-ethanol mixture (volume ratio of 1:3). The resulting suspension was left for 20 minutes and then filtered through a glass filter to take up a "purified filtrate". The above "purified filtrate" was concentrated under reduced pressure to obtain a solid residue. Since the phospholipid content of the residue was found to be 68.3%, 820 mg of dipalmitoylphosphatidylcholine was added to 1,000 mg of the solid residue, and the mixture was suspended in sterile distilled water and then lyophilized to produce a white powder of the active material of the invention (1,730 mg).

tension ranges of the material estimated by Wilhelmy's method wherein the material is added dropwise to the surface of physiological saline in an amount of 0.3–0.8 μg per square centimeter of surface area thereof being 2.1–8.6 dynes/cm and 48.2–58.0 dynes/cm when surface areas are 21.0 cm$^2$ and 45.6 cm$^2$ respectively.

2. Surface active material as claimed in claim 1, wherein the phospholipid content is estimated by multiplying its phosphorous content by 25; the individual contents of neutral lipid, total cholesterol carbohydrate and protein being expressed by calculating in respectively glycerol trioleate equivalent, cholesterol equivalent, glucose equivalent and bovine serum albumin equivalent.

3. Surface active material as claimed in claim 2, wherein the phospholipid content consists mainly of phosphatidylcholine and phosphatidylglycerol, the contents of which are 63.0–85.5% and 3.0–12.0% respectively, both based on the total weight of phospholipid content.

4. Surface active material as claimed in claim 3, wherein the content of phosphatidylcholine having two saturated fatty acid residues based on the total weight of phosphatidylcholine is 67.5–90.3%.

5. Surface active material as claimed in claim 4, wherein one of the saturated fatty acid residues is palmitic acid residue.

6. Surface active material as claimed in any one of claims 1, 2, 3, 4 or 5 wherein the mammal is selected from the group consisting of cattle, horses, sheep and pigs.

7. A pharmaceutical composition useable for the treatment of hyaline-membrane disease comprising an effective amount of surface-active material as set forth in claim 1 and a pharmaceutically acceptable non-toxic carrier thereof.

8. A pharmaceutical composition as claimed in claim 7, wherein the effective amount for a mammal is between about 50 and 400 milligrams per one treatment.

9. A pharmaceutical composition according to claim 7, wherein the carrier is selected from the group consisting of water and electrolyte solution.

10. A pharmaceutical composition according to claim 9, wherein the electrolyte solution is physiological saline.

TABLE V

| Example Nos. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Composition of the material (%) | | | | | | | | | | | | | | | |
| Phospholipid | 81.6 | 87.5 | 86.4 | 85.9 | 90.2 | 86.5 | 89.6 | 83.2 | 95.5 | 94.0 | 94.5 | 94.7 | 75.0 | 76.1 | 83.3 |
| Neutral lipid | 10.6 | 5.2 | 7.1 | 7.8 | 3.0 | 4.2 | 3.6 | 10.9 | 1.8 | 1.1 | 2.0 | 1.6 | 14.0 | 10.8 | 7.9 |
| Total cholesterol | 2.3 | 0.9 | 1.2 | 1.0 | 0.5 | 0.6 | 2.1 | 1.5 | 0.0 | 0.3 | 0.3 | 0.2 | 3.0 | 2.5 | 1.1 |
| Carbohydrate | 1.2 | 0.2 | 1.1 | 0.9 | 0.9 | 0.7 | 0.2 | 0.4 | 0.2 | 0.5 | 0.1 | 0.1 | 0.7 | 1.5 | 0.8 |
| Protein | 2.3 | 1.2 | 2.0 | 1.4 | 1.7 | 2.5 | 0.7 | 1.3 | 0.5 | 0.9 | 1.6 | 1.2 | 5.0 | 3.1 | 1.8 |
| Water | 2.3 | 5.1 | 2.1 | 3.5 | 4.0 | 5.2 | 3.8 | 2.8 | 2.9 | 3.8 | 1.7 | 2.0 | 3.3 | 6.0 | 4.6 |
| Ratio of phospholipid content to protein content | 35.5 | 72.9 | 43.2 | 59.5 | 53.1 | 34.6 | 128.0 | 64.0 | 191.0 | 104.4 | 59.1 | 78.9 | 15.0 | 24.5 | 46.3 |
| Composition of phospholipid (%) | | | | | | | | | | | | | | | |
| Phosphatidylcholine | 74.6 | 81.3 | 72.6 | 72.8 | 73.6 | 73.1 | 71.5 | 71.9 | 78.3 | 69.5 | 70.6 | 75.2 | 63.0 | 74.2 | 85.5 |
| Phosphatidylglycerol | 10.6 | 4.5 | 10.3 | 12.0 | 8.6 | 9.0 | 11.3 | 10.2 | 3.0 | 8.6 | 6.4 | 7.9 | 11.9 | 11.7 | 3.5 |
| Phosphatidylethanolamine | 3.8 | 4.8 | 4.3 | 4.2 | 6.2 | 5.1 | 5.3 | 7.3 | 7.5 | 6.2 | 7.6 | 5.6 | 7.7 | 5.1 | 2.5 |
| Sphingomyelin | 5.7 | 5.7 | 5.9 | 5.7 | 6.0 | 6.5 | 5.7 | 6.0 | 6.5 | 6.0 | 7.0 | 6.3 | 7.0 | 6.3 | 5.9 |
| Phosphatidylinositol and Phosphatidylserine | 3.8 | 3.8 | 4.2 | 4.4 | 4.8 | 6.0 | 4.3 | 4.2 | 3.9 | 7.4 | 6.1 | 4.1 | 7.3 | 3.5 | 2.4 |
| Lysophosphatidylcholine | 0.8 | 0.5 | 2.1 | 0.6 | 1.3 | 0.8 | 0.6 | 0.5 | 1.1 | 1.2 | 2.1 | 0.8 | 2.1 | 1.9 | 0.5 |
| Others | 0.3 | 0.2 | 0.2 | 0.1 | 0.1 | 0.5 | 0.3 | 0.1 | 0.4 | 1.0 | 0.7 | 0.8 | 1.0 | 0.4 | 0.0 |
| Content of phosphatidylcholine having two saturated fatty acid residues based on the total phosphatidylcholine (%) | 83.5 | 88.6 | 89.2 | 86.2 | 83.3 | 82.1 | 84.3 | 88.6 | 79.8 | 78.8 | 83.1 | 80.6 | 67.5 | 86.2 | 90.3 |

What is claimed is:

1. Surface active material containing phospholipid, neutral lipid, total cholesterol, carbohydrate, protein and water, which material is obtained from lung tissue of a mammal with or without further phospholipid, characterized in that the phospholipid content is 75.0–95.5%, the neutral lipid content is 1.8–14.0%, the total cholesterol content is 0.0–3.0%, the carbohydrate content is 0.1–1.5%, the protein content is 0.5–5.0% and water content is 1.7–6.0%, all based on the dried weight of said material, the minimum and maximum surface 11. A pharmaceutical composition according to claim 7, wherein the effective amount is administered directly into an airway of a mammal suffering from hyaline-membrane disease.

12. A pharmaceutical composition according to claim 11, wherein the effective amount is administered in a suspension form.

13. A method of producing a surface active material containing phospholipid, neutral lipid, total cholesterol, carbohydrate, protein and water, which material is obtained from lung tissue of a mammal with or without further phospholipid, characterized in that the phospholipid content is 75.0–95.5%, the neutral lipid content is 1.8–14.0%, the total cholesterol content is 0.0–3.0%, the carbohydrate content is 0.1–1.5%, the protein content is 0.5–5.0% and water content is 1.7–6.0%, all based on the dried weight of said material, the minimum and maximum surface tension ranges of the material estimated by Wilhelmy's method wherein the material is added dropwise to the surface of physiological saline in an amount of 0.3–0.8 g per square centimeter of surface area thereof being 2.1–8.6 dynes/cm and 48.2 to 58.0 dynes/cm when surface areas are 21.0 cm$^2$ and 45.6 cm$^2$ respectively, comprising the steps of:

(a) mincing lung tissue of a mammal;
(b) bringing the minced lung tissue into contact with an electrolyte solution and subjecting the resultant mixture to one of filtration under pressure and centrifugation at about 500–1,500 rpm to obtain an extract;
(c) centrifuging the extract at about 12,000–16,000 rpm to obtain a crude sediment;
(d) forming an aqueous suspension of the crude sediment and dissolving sodium chloride in the aqueous suspension of the crude sediment to obtain a density adjusted suspension and then centrifuging the adjusted suspension at about 4,000–10,000 rpm so as to divide it into three layers, the top layer being an emulsified scum layer which is then taken up;
(e) forming an aqueous suspension of the top layer and dialyzing the aqueous suspension through a semi-permeable membrane to remove inorganic salts and water-soluble organic compounds of low molecular weight both having been remained in the top layer, whereby an aqueous suspension containing the non-dialyzing material is obtained;
(f) centrifuging the resultant suspension at about 12,000–16,000 rpm to take up a pure sediment;
(g) suspending one of the pure sediments and the aqueous suspension containing the non-dialyzing material, in an aqueous sucrose solution and centifuging the suspension of aqueous sucrose solution at about 18,000–40,000 rpm to obtain another pure sediment;
(h) drying the pure sediment and suspending the resultant dried pure sediment in acetone to take up an acetone-insoluble material which is then dried and suspended further in organic solvent mixture followed by filtration of the resultant suspension so as to obtain a purified filtrate; and
(i) mixing the purified filtrate with sterile water and subjecting the resultant mixture to filtration, the filtrate of which is then concentrated under reduced pressure to obtain a solid residue, followed by one of lyophilization of the said solid residue so that the phospholipid content is 75.0–95.5% or adding further phospholipid solid residue to bring the phospholipid content to 75.0–95.5%.

14. Method as claimed in claim 13, wherein the mincing is performed by using a meat-grinder.

15. Method as claimed in claim 13, wherein the minced lung tissue before being used is lyophilized and then preserved.

16. Method as claimed in claim 13, wherein the electrolyte solution is physiological saline.

17. Method as claimed in claim 13, wherein the density of the adjusted suspension of step (d) has a value of 1.07–1.20.

18. Method as claimed in claim 13, wherein the semipermeable membrane is selected from the group consisting of cellophane membrane, collodion membrane and bladder membrane.

19. Method as claimed in claim 13, wherein one part of the dried pure sediment of step (h) is suspended in 100–300 parts of acetone at $-10°-+10°$ C.

20. Method as claimed in claim 13, wherein one part of the dried acetone-insoluble material of step (h) is suspended in 100–300 parts of organic solvent mixture.

21. Method as claimed in claim 20, wherein the organic solvent mixture is selected from the group consisting of chloroform-methanol with a 2:1 volume ratio, chloroform-ethanol with a 2:1 volume ratio, chloroform-isopropanol with a 1:1 volume ratio and ethyl ether-ethanol with a 3:1 volume ratio.

22. Method as claimed in claim 13, wherein the further phospholipid is selected from the group consisting of phosphatidylglycerol, phosphatidylcholine having two saturated fatty acid residues, and a mixture thereof.

23. Method as claimed in claim 22, wherein the saturated fatty acid residue is palmitic acid residue.

* * * * *